(12) United States Patent
Gangjee et al.

(10) Patent No.: US 10,167,287 B2
(45) Date of Patent: Jan. 1, 2019

(54) SUBSTITUTED PYRIMIDINE COMPOUNDS AND METHODS OF USE AND MANUFACTURE

(71) Applicants: Duquesne University of the Holy Spirit, Pittsburgh, PA (US); Wayne State University, Detroit, MI (US)

(72) Inventors: Aleem Gangjee, Allison Park, PA (US); Larry H. Matherly, Novi, MI (US)

(73) Assignee: Duquesne University of the Holy Spirit, Pittsburgh, PA (US)

( * ) Notice: Subject to any disclaimer, the term of this patent is extended or adjusted under 35 U.S.C. 154(b) by 0 days.

(21) Appl. No.: 15/479,938

(22) Filed: Apr. 5, 2017

(65) Prior Publication Data
US 2017/0260190 A1 Sep. 14, 2017

Related U.S. Application Data

(62) Division of application No. 14/820,646, filed on Aug. 7, 2015, now Pat. No. 9,650,384.

(60) Provisional application No. 62/035,208, filed on Aug. 8, 2014.

(51) Int. Cl.
*C07D 487/04* (2006.01)
*C07D 239/70* (2006.01)

(52) U.S. Cl.
CPC ......... *C07D 487/04* (2013.01); *C07D 239/70* (2013.01)

(58) Field of Classification Search
USPC ...................................................... 544/280
See application file for complete search history.

(56) References Cited

U.S. PATENT DOCUMENTS 6,103,727 A 8/2000 Gangjee

FOREIGN PATENT DOCUMENTS

EP 0010312 4/1980

OTHER PUBLICATIONS

Gonen et. al. (Drug resistance Updates, 2012, 15:183-210). (Year: 2012).*
Gura et. al. (Science, 1997, 278:1041-1042). (Year: 1997).*
Johnson et. al. (British Journal of Cancer, 2001, 84:1424-1431). (Year: 2001).*
J. G. Cannon, Chapter Nineteen in Burger's Medicinal Chemistry and Drug Discovery, Fifth Edition, vol. I: Principles and Practice, Wiley-Interscience 1995, pp. 783-802. (Year: 1995).*
Mitchell-Ryan et. al (Journal of Medicinal Chemistry (2013) 56:100016-10032), (Year: 2013).*
Mitchell-Ryan, S. et al., "Discovery of 5-Substituted Pyrrolo[2,3 d]pyrimidine Antifolates as Dual-Acting Inhibitors of Glycinamide Ribonucleotide Formyltransferase adn 5-Aminomidazole-4-carboxamide Ribonucleotide Formyltransferase in De Novo Purine Nucleotide Biosynthesis: Implications of Inhibiting 5-Aminoimidazole-4-carboxamide Ribonucleotide Formyltransferase to AMPK Activation and Antihumor Activity", Journal of Medicinal Chemistry, 2013, vol. 56, 10016-10032, American Chemical Society.
Gangjee, A. et al., "Synthesis and Discovery of Water-Soluble Microtubule Targeting Agents that Bind to the Colochicine Site on Tubulin and Circumvent Pgp Mediated Resistance", Journal of Medicinal Chemistry, 2010, vol. 53, 8116-8128, American Chemical Society.
Kaburagi, Y. et al., "Total Synthesis of (−)-Strychnine", Journal of American Chemical Society, 2004, vol. 126, 10246-10247, American Chemical Society.
Lowe, J.T. et al., "Synthesis and Profiling of a Diverse Collection of Azetidine-Based Scaffolds for the Development of CNS-Focused Lead-like Libraries", Journal of Organic Chemistry, 2012, vol. 77, 7187-7211, American Chemical Society.
International Search Report and Written Opinion for PCT/2015/044139 dated Nov. 4, 2015.
Gura et al. (Science, 1997, 278:1041-1042).
Johnson et al. (British Journal of Cancer, 2001, 84:1424-1431).
J.G. Cannon, Chapter Nineteen in Burger's Medicinal Chemistry and Drug Discovery, Fifth Edition, vol. 1: Principles and Practice, Wiley-Interscience 1995, pp. 783-802.

* cited by examiner

*Primary Examiner* — Marcos L Sznaidman
(74) *Attorney, Agent, or Firm* — Eckert Seamans Cherin & Mellott, LLC; Carol A. Marmo (57) ABSTRACT

This invention provides substituted pyrimidine compounds having the formula:

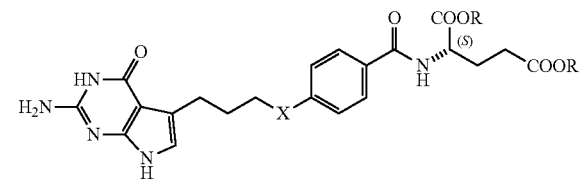

wherein X is absent, $CH_2$, S, or O, and R is an alkyl group having from one to ten carbon atoms, and optionally salts, hydrates, or solvates thereof, that are useful in treating a patient having a disease or cancer. The compounds of this invention are useful as multi-enzyme antifolates selectively targeting the folate receptor (FR). Further, a method of making 5- and 6-substituted cyclopenta[d]pyrimidine for nonclassical and classical antifolates as TS and DHFR inhibitors is provided.

1 Claim, 3 Drawing Sheets

SUBSTITUTED PYRIMIDINE COMPOUNDS AND METHODS OF USE AND MANUFACTURE

CROSS-REFERENCE TO RELATED APPLICATION

This divisional patent application claims the benefit of pending U.S. patent application Ser. No. 14/820,646, filed on Aug. 7, 2015, which claims the benefit of U.S. Provisional Patent Application Ser. No. 62/035,208, filed Aug. 8, 2014. The entire contents of U.S. patent application Ser. Nos. 14/820,646 and 62/035,208 are incorporated by reference into this divisional patent application as if fully written herein.

STATEMENT REGARDING FEDERALLY SPONSORED RESEARCH

This invention was made with government support under grant numbers RO1CA166711, CA125153, CA152316, and CA53535 awarded by the National Institutes of Health, National Cancer Institute. The government has certain rights in the invention.

BACKGROUND OF THE INVENTION

1. Field of the Invention

This invention provides substituted pyrimidine compounds that are useful in treating a patient having cancer. The compounds of this invention are useful as multi-enzyme antifolates selectively targeting the folate receptor (FR). Further, a method of making 5- and 6-substituted cyclopenta[d]pyrimidine for nonclassical and classical antifolates as TS and DHFR inhibitors is provided.

2. Description of the Background Art

Folates are indispensable for cell growth and tissue regeneration. Mammalian cells do not synthesize folates de novo and rely on extracellular folates taken up by three major folate uptake systems: (1) The main transport system at physiologic pH is the reduced folate carrier (RFC or SLC19A1). RFC is a member of the major facilitator superfamily of transporters and functions as anion anti-porter; (2) Folate receptors (FRs) α and β are glycosyl phosphatidylinositol-anchored proteins that transport folates by endocytosis.[1,2] Compared to RFC, folate uptake by FRs shows restricted tissue distribution. Several tumor cell lines express FRs (kidney, ovary, thymus and others); (3) The third transport system is a proton-folate symporter that functions optimally at acidic pH-proton-coupled folate transporter (PCFT; SLC46A1).[3-5]

Figure 1:
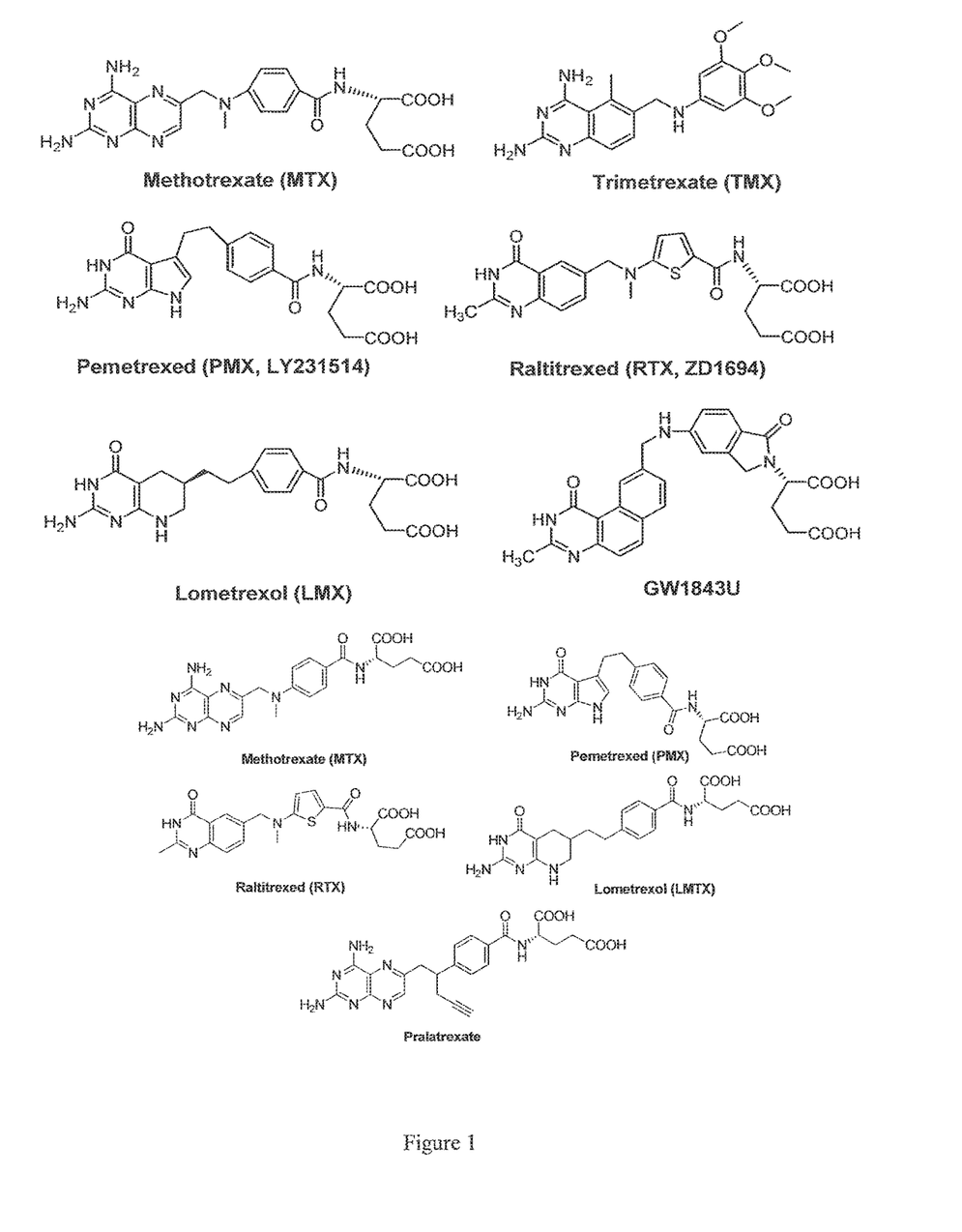
FIG. 1 shows the structures of known classical antifolate compounds.

Antifolates that target folate-dependent biosynthetic pathways function as anti-proliferative agents. Potent inhibitors of a) dihydrofolate reductase (DHFR) [methotrexate (MTX)], b) thymidylate synthase (TS) [raltitrexed (RTX), GW1843U, pemetrexed (PMX)], c) β-glycinamide ribonucleotide formyl transferase (GARFTase) [lometrexol (LMX), PMX] and d) 5-aminoimidazole-4-carboxamide ribonucleotide formyl transferase (AICARFTase) [PMX] are all antifolate drugs that are used in cancer chemotherapy or have been clinically evaluated.[6-8] Figure1 shows the chemical structures of known clinically evaluated and available antifolate compounds. All of the clinically available antifolates are transported by RFC, a ubiquitously expressed folate transporter, and hence suffer from dose-limiting toxicity which is a major obstacle in the chemotherapy of cancer.[8-9] As such, it is desirable to design targeted antifolates that are selectively taken up by transport systems (other than RFC) which have limited expression and function in normal tissues compared with tumors. Additionally, designing drugs that inhibit multiple enzymes in both purine and pyrimidine pathways can circumvent problems of enzyme and consequent tumor resistance.

FIG. 1 shows the structures of known classical antifolates including Methotrexate (MTX), Pemetrexed (PMX), Raltitrexed (RTX), Lometrexol (LMTX) and Pralatrexate.

The antifolates are a class of antiproliferatives widely recognized for their inhibition of folate metabolism. Major antifolate enzyme targets include thymidylate synthase (TS) and dihydrofolate reductase (DHFR). Inhibition of these enzymes suppresses de novo nucleotide biosynthesis, resulting in an imbalance of purine and pyrimidine precursors and rendering cells incapable of undergoing accurate DNA replication, ultimately resulting in cell death. Clinically relevant TS (e.g., pemetrexed, PMX) and DHFR (e.g., methotrexate (MTX) and pralatrexate) inhibitors (see FIG. 1) continue to play important roles in treating hematologic malignancies and solid tumors.[13,14]

Antifolates targeting de novo purine nucleotide biosynthesis were also described and include lometrexol ((6R)5,10-dideazatetrahydrofolate, LMTX) (FIG. 1), (2S)-2-((5-(2-((6R)-2-amino-4-oxo-5,6,7,8-tetrahydro-1H-pyrido[2,3-d]pyrimidin-6-yl)ethyl)thiophene-2-carbonyl)amino) pentanedioic acid (LY309887), and (2S)-2-((5-(2-((6S)-2-amino-4-oxo-1,6,7,8-tetrahydropyrimido[5,4-b]ate][1,4]thiazin-6-yl)ethyl)thiophene-2-carbonyl)amino) pentanedioic acid (AG2034). All of these drugs inhibit the first folate-dependent step in purine nucleotide biosynthesis, catalyzed by β-glycinamide ribonucleotide (GAR) formyltranferase (GARFTase), and have progressed to clinical trials.[16,17] However, their toxicities were dose-limiting, most likely a consequence of their cellular uptake and metabolism to polyglutamates in normal tissues.

The reduced folate carrier (RFC) is one of three mechanisms of (anti)folate uptake into mammalian cells. Cellular requirements for folate cofactors for DNA replication provide a plausible explanation for the high levels of RFC in most tumors. However, demands for folates, and consequently RFC, are also shared by normal tissues such that RFC may not be the optimal mechanism for tumor-selective uptake of cytotoxic folate analogues.[15] Other cellular uptake mechanisms, notably, the proton-coupled folate transporter (PCFT) and folate receptors (FRs) α and β, are also expressed in tumors and show more restricted expression in normal tissues.[16,17] Furthermore, PCFT is a proton symporter such that in the acidic microenvironment generated by glycolytic tumors, membrane transport and selective tumor targeting by this mechanism is enhanced. For FRα, the apical spatial orientation in normal epithelial tissues is often disrupted in tumors such that its basolateral membrane expression in tumors results in exposure to the circulation. These features provide a compelling rationale for developing folate-based therapeutics that target PCFT and FRα for cancer therapy. Examples of FRα-targeted therapies include a monoclonal antibody, Farletuzumab (Morphotech), a cytotoxic folate conjugate, Vintafolide (EC145; Endocyte), and, ONX0801, a classical antifolate that is selectively transported into cells by FRs over RFC and inhibits de novo thymidylate biosynthesis.[15,18]

SUMMARY OF THE INVENTION

In one embodiment of this invention, a compound is provided having the formula:

wherein X is O or S and n is an integer ranging from one to three, and optionally comprising a pharmaceutically acceptable salt or hydrate thereof.

In another embodiment of this invention, a compound is provided having the formula:

wherein X is absent, CH$_2$, O, or S, and R is an alkyl group having from one to ten carbon atoms or a hydrogen, and optionally comprising a pharmaceutically acceptable salt or hydrate thereof.

In another embodiment of this invention, a compound is provided having the formula:

wherein X is absent, CH$_2$, O, or S, and R is an alkyl group having from one to ten carbon atoms, and optionally comprising a pharmaceutically acceptable salt or hydrate thereof.

In another embodiment of this invention, a compound is provided having the formula:

and optionally comprising a pharmaceutically acceptable salt or hydrate thereof.

In another embodiment of this invention, the compounds as disclosed herein include a pharmaceutically acceptable solvate thereof.

In another embodiment of this invention, a pharmaceutical composition is provided comprising a therapeutically effective amount of a compound of the formula:

wherein X is O or S and n is an integer ranging from one to three, and optionally comprising a pharmaceutically acceptable salt or hydrate thereof.

In another embodiment of this invention, a pharmaceutical composition is provided comprising a therapeutically effective amount of a compound of the formula:

wherein X is absent, CH$_2$, O, or S, and R is an alkyl group having from one to ten carbon atoms or a hydrogen, and optionally comprising a pharmaceutically acceptable salt or hydrate thereof.

In another embodiment of this invention, a pharmaceutical composition is provided comprising a therapeutically effective amount of a compound of the formula:

wherein X is absent, CH$_2$, O, or S, and R is an alkyl group having from one to ten carbon atoms, and optionally comprising a pharmaceutically acceptable salt or hydrate thereof.

In another embodiment of this invention, a pharmaceutical composition is provided comprising a therapeutically effective amount of a compound of the formula:

and optionally comprising a pharmaceutically acceptable salt or hydrate thereof.

In another embodiment of this invention, the pharmaceutical compositions as disclosed herein are provided comprising at least one pharmaceutically acceptable carrier.

In another embodiment of this invention, a method is provided for treating a patient having cancer comprising administering to a patient an effective amount of a compound comprising formula:

wherein X is O or S and n is an integer ranging from one to three, and optionally comprising a pharmaceutically acceptable salt, hydrate, or solvate thereof, and including optionally administering an effective amount of the salt, hydrate, or solvate of the compound to the patient.

In another embodiment of this invention, a method is provided for treating a patient having cancer comprising administering to a patient an effective amount of a compound comprising formula:

wherein X is absent, CH$_2$, O, or S, and R is an alkyl group having from one to ten carbon atoms or a hydrogen, and optionally comprising a pharmaceutically acceptable salt, hydrate, or solvate thereof, and including optionally administering an effective amount of the salt, hydrate, or solvate of the compound to the patient.

In another embodiment of this invention, a method is provided for treating a patient having cancer comprising administering to a patient an effective amount of a compound comprising formula:

wherein X is absent, CH$_2$, O, or S, and R is an alkyl group having from one to ten carbon atoms, and optionally comprising a pharmaceutically acceptable salt, hydrate, or solvate thereof, and including optionally administering an effective amount of the salt, hydrate, or solvate of the compound to the patient.

In another embodiment of this invention, a method is provided for treating a patient having cancer comprising administering to a patient an effective amount of a compound comprising formula:

and optionally comprising a pharmaceutically acceptable salt, hydrate, or solvate thereof, and including optionally administering an effective amount of the salt, hydrate, or solvate of the compound to the patient.

Yet, in another embodiment of this invention, a method of treating a patient having a disease comprising administering to a patient an effective amount of one or more compounds of this invention, is provided. The method includes administering an effective amount of a salt or a hydrate or a solvate of at least one of the compound(s) of this invention to the patient.

In another embodiment of this invention, 5- and 6-substituted cyclopenta[d]pyrimidine compounds are provided, and in another embodiment of this invention, a method of making the 5- and 6-substituted cyclopenta[d]pyrimidines for nonclassical and classical antifolates is provided. The 5- and 6-substituted cyclopenta[d]pyrimidines are useful as antifolate compounds.

DETAILED DESCRIPTION OF THE INVENTION

The present invention provides multi-enzyme anti-folate compounds selectively targeting the folate receptor (FR).

In one embodiment of this invention, a compound is provided having the formula:

wherein X is O or S and n is an integer ranging from one to three, and optionally comprising a pharmaceutically acceptable salt or hydrate thereof.

In another embodiment of this invention, a compound is provided having the formula:

wherein X is absent, $CH_2$, O, or S, and R is an alkyl group having from one to ten carbon atoms or a hydrogen, and optionally comprising a pharmaceutically acceptable salt or hydrate thereof.

In another embodiment of this invention, a compound is provided having the formula:

wherein X is absent, $CH_2$, O, or S, and R is an alkyl group having from one to ten carbon atoms, and optionally comprising a pharmaceutically acceptable salt or hydrate thereof.

In another embodiment of this invention, a compound is provided having the formula:

and optionally comprising a pharmaceutically acceptable salt or hydrate thereof.

In another embodiment of this invention, the compounds as disclosed herein include a pharmaceutically acceptable solvate thereof.

In another embodiment of this invention, a pharmaceutical composition is provided comprising a therapeutically effective amount of a compound of the formula:

wherein X is O or S and n is an integer ranging from one to three, and optionally comprising a pharmaceutically acceptable salt or hydrate thereof.

In another embodiment of this invention, a pharmaceutical composition is provided comprising a therapeutically effective amount of a compound of the formula:

wherein X is absent, CH$_2$, O, or S, and R is an alkyl group having from one to ten carbon atoms or a hydrogen, and optionally comprising a pharmaceutically acceptable salt or hydrate thereof.

In another embodiment of this invention, a pharmaceutical composition is provided comprising a therapeutically effective amount of a compound of the formula:

wherein X is absent, CH$_2$, O, or S, and R is an alkyl group having from one to ten carbon atoms, and optionally comprising a pharmaceutically acceptable salt or hydrate thereof.

In another embodiment of this invention, a pharmaceutical composition is provided comprising a therapeutically effective amount of a compound of the formula:

and optionally comprising a pharmaceutically acceptable salt or hydrate thereof.

In another embodiment of this invention, the pharmaceutical compositions as disclosed herein are provided comprising at least one pharmaceutically acceptable carrier.

In another embodiment of this invention, a method is provided for treating a patient having cancer comprising administering to a patient an effective amount of a compound comprising formula:

wherein X is O or S and n is an integer ranging from one to three, and optionally comprising a pharmaceutically acceptable salt, hydrate, or solvate thereof, and including optionally administering an effective amount of the salt, hydrate, or solvate of the compound to the patient.

In another embodiment of this invention, a method is provided for treating a patient having cancer comprising administering to a patient an effective amount of a compound comprising formula:

wherein X is absent, $CH_2$, O, or S, and R is an alkyl group having from one to ten carbon atoms or a hydrogen, and optionally comprising a pharmaceutically acceptable salt, hydrate, or solvate thereof, and including optionally administering an effective amount of the salt, hydrate, or solvate of the compound to the patient.

In another embodiment of this invention, a method is provided for treating a patient having cancer comprising administering to a patient an effective amount of a compound comprising formula:

wherein X is absent, $CH_2$, O, or S, and R is an alkyl group having from one to ten carbon atoms, and optionally comprising a pharmaceutically acceptable salt, hydrate, or solvate thereof, and including optionally administering an effective amount of the salt, hydrate, or solvate of the compound to the patient.

In another embodiment of this invention, a method is provided for treating a patient having cancer comprising administering to a patient an effective amount of a compound comprising formula:

and optionally comprising a pharmaceutically acceptable salt, hydrate, or solvate thereof, and including optionally administering an effective amount of the salt, hydrate, or solvate of the compound to the patient.

A method of treating a patient having a disease comprising administering to a patient an effective amount of one or more compounds of this invention. The method includes administering an effective amount of a salt or a hydrate or a solvate of at least one of the compound(s) of this invention to the patient.

In another embodiment of this invention, 5- and 6-substituted cyclopenta[d]pyrimidine compounds are provided, and in another embodiment of this invention, a method of making the 5- and 6-substituted cyclopenta[d]pyrimidines for nonclassical and classical antifolates are provided. In a preferred embodiment, the method of synthesizing a cyclopenta[d]pyrimidine has an ethoxycarbonyl group attached at either the 5- or 6-position of the cyclopenta[d]pyrimidine. The method of making the 5- and 6-substituted cyclopenta[d]pyrimidines of this invention comprises: treating a tricarboxylic acid compound with oxalyl chloride and a catalytic amount of DMF to achieve a tricarbonyl chloride compound; providing triethyl esterification of said tricarbonyl chloride compound with anhydrous ethanol in toluene to achieve a triethyl carboxylate compound; providing cyclization of said triethyl carboxylate compound with sodium ethoxide in toluene to achieve a mixture of diethoxycarbonyl cyclopentone compounds; providing cyclization of the mixture of said diethoxycarbonyl cyclopentone compounds with acetamidine to afford a mixture of cyclopenta[d]pyrimidine compounds; reduction of an ester moieties in said mixture of said cyclopenta[d]pyrimidine compounds with DIBALH at −30° C. to form a reduced mixture of said cyclopenta[d]pyrimidines and separating said reduced mixture of said cyclopenta[d]pyrimidines into a higher polarity cyclopenta[d]pyrimidine compound and a lower polarity cyclopenta[d]pyrimidine compound; subjecting the lower polarity cyclopenta[d]pyrimidine compound to nosylation with NsCl and TEA and catalytic DMAP in DCM to afford a dinosylated compound; providing selective nucleophilic displacement of the 6-Ns in said dinosylated compound with ethyl 4-hydroxy benzoic acid ester, cesium carbonate and molecular sieves in acetonitrile to form a pteroic ester compound; hydrolysis of said pteroic acid compound with 1N KOH to yield pteroic acid; providing peptide coupling of said pteroic acid with L-glutamic acid ester and coupling reagents CDMT and NMM in DMF and performing hydrolysis in 1N NaOH to provide a cyclopenta[d]pyrimidine having an ethoxycarbonyl group attached at either the 5- or 6-position of the cyclopenta[d]pyrimidine. The 5- and 6-substituted cyclopenta[d]pyrimidine compounds of this invention are TS (thymidylate synthase) and DHFR (dihydrofoate reductase) inhibitors.

As used herein, the term "effective amount" is defined as the amount of a compound or composition required to effect a particular result, such as for example, but not limited to, treating a patient for a disease, including cancer.

As used herein, the term "patient" includes all members of the animal kingdom, including but not limited to, *Homo sapiens*, warm and cold blooded animals, and reptiles.

The compounds of this application may be administered to a patient in any suitable pharmaceutical form, with or in any suitable pharmaceutical carrier, and via a suitable route of administration, including for example, but not limited to, the oral route, buccal route, rectal route, parenteral route, intraperitoneal route, intramuscular route, ophthalmic route, dermal route, and inhalation route, to name a few. A pharmaceutically acceptable carrier is any such carrier known to those persons skilled in the art and may include for example but is not limited to saline, dextrose in water, starch, talc, dextrose, or sucrose, and the like.

Figure 2:
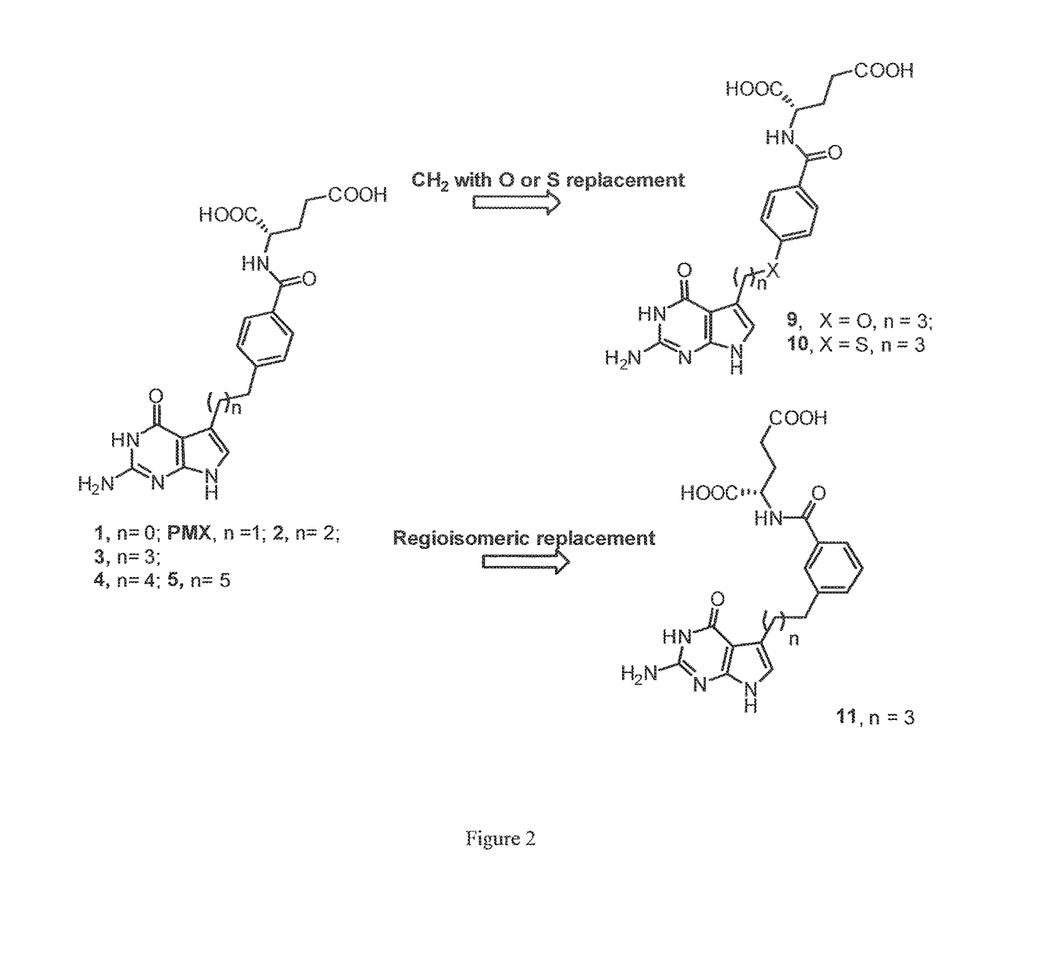
FIG. 2 shows heteroatom replacement of the benzylic carbon and regioisomeric substitution on the phenyl ring to explore the SAR of multiple enzyme inhibition and FR uptake.

FIG. 2 shows the structures of compounds 1-5 as discussed in Table1, below:

TABLE 1

$IC_{50}$ values (nM) for 5-substituted pyrrolo[2,3-d]pyrimidine antifolates and classical antifolate PMX in RFC-, PCFT-, and FR-expressing cell lines[a]. The data shown are mean values from 3 to 10 experiments (±standard errors in parentheses). The results are presented as $IC_{50}$ values corresponding to the concentrations that inhibit growth by 50% relative to cells incubated without drug.

|  | KB (nM) | PC43-10, RFC (nM) | R2 (nM) | RT16, FR (nM) | PCFT (nM) |
|---|---|---|---|---|---|
| PMX (n = 1) | 9.94 (3.11) | 30.6 (6.2) | >1000 | 18.2 (3.8) | 22.3 (8.6) |
| 1 (n = 0) | >1000 | >1000 | >1000 | >1000 | >1000 |
| 2 (n = 2) | 49.5 (13.2) | 68.8 (21.2) | >1000 | 72.0 (27.1) | 329 (61) |
| 3 (n = 3) | 12.7 (5.4) | 56.6 (5.8) | >1000 | 8.6 (2.1) | 840 (90) |
| 4 (n = 4) | 17.3 (8.9) | 196.4 (55) | >1000 | 33.5 (2.5) | 898 (102) |
| 5 (n = 5) | >1000 | >1000 | >1000 | >1000 | >1000 |

[a]Growth inhibition assays were performed for CHO sublines engineered to express human RFC (PC43-10), FRα (RT16), or PCFT (R2/PCFT4) for comparison with transporter-null (R2 and R2(VC)) CHO cells and for the KB human tumor subline (expressing RFC, FRα, and pcft)

Recently[1] we reported a series of PMX homologs, 5-substituted pyrrolo[2,3-d]pyrimidine phenyl antifolates 1-5 (see FIG. 2).

Compound 3 was the most active KB tumor cell inhibitor of this series. It was transported into tumor cells by folate receptors (FRs) and it inhibited two of the folate cofactor utilizing de novo purine biosynthesis enzymes, AICAR-FTase and GARFTase.[1] To further explore the SAR of 5-aminoimidazole-4-carboxamide ribonucleotide and glycinamide ribonucleotide formyltransferase (AICARFTase and GARFTase, respectively) dual enzyme inhibition and FR targeted specificity, this invention provides novel compounds and synthesis thereof.

A 4 carbon containing linker provided the optimum chain length required for multiple enzyme inhibition and showed that the distance between the pyrrolo[2,3-d]pyrimidine scaffold and the glutamic acid side chain is critical for both FR transport and multiple enzymes targeting. A design strategy was implemented to further probe the importance of distance, as well as relative alignment of the pyrrolo[2,3-d]pyrimidine and glutamic acid portions, by synthesizing novel compounds 9-11 of this invention. This strategy may alter the shape of the molecule for a better fit in the binding region as can be gleaned from compounds 9 and 11 and/or increase the chain length above that of compound 3 and below that of compound 4 as in novel compound of this invention 10. This strategy aims to further define the importance of the bridge chain length and the bridge conformation for optimum activity and selectivity.

Syntheses

Scheme 1

-continued

Scheme 2

Condensation of α-bromo aldehyde with 2,4-diamino-4-oxo-pyrimidine 19 is the key step in the synthesis of compounds 9-11 as outlined in Scheme 1 and Scheme 2. Commercially available alcohol 14 was coupled to the corresponding phenyl esters and oxidized to the corresponding aldehydes 17a and 17b (Scheme 1).[9t] Alcohol 24 was coupled to the appropriate phenyl ester to afford the aldehyde 25 (Scheme 2). The aldehydes were reacted with Br₂ in dioxane to give the desired α-bromoaldehydes[12] 18a, 18b (Scheme 1) and 26 (Scheme 2) and immediately reacted with 2,4-diamino-6-hydroxypyrimidine 19 to cyclize to the 5-substituted pyrrolo[2,3-d]pyrimidines 20a, 20b (Scheme 1) and 27 (Scheme 2).[1] Hydrolysis of the esters provided the free acids 21a, 21b and 28. Subsequent peptide coupling with diethyl L-glutamate using the activating agents N-methyl morpholine and 2,4-dimethoxy-6-chlorotriazine, afforded the diesters 22a, 22b and 29. Saponification of the diesters yielded the final compounds 9-11 of this invention.

TABLE 2

IC$_{50}$ values (nM) for 5-substituted pyrrolo[2,3-d]pyrimidine antifolates and classical antifolate PMX in RFC-, PCFT-, and FR-expressing cell lines.

|   | KB (nM) | PC43-10, RFC (nM) | R2 (nM) | RT16, FR (nM) | PCFT (nM) |
|---|---|---|---|---|---|
| X (n = 1) | 9.94 (3.11) | 30.6 (6.2) | >1000 | 18.2 (3.8) | 22.3 (8.6) |
| 3 (n = 3) | 12.7 (5.4) | 56.6 (5.8) | >1000 | 8.6 (2.1) | 840 (90) |
| 9 | 51.02 | 53.2 | >1000 | 42.17 | 390 |
| 10 | >1000 | >1000 | >1000 | 281 | 549 |
| 11 | >1000 | 608 | >1000 | >1000 | >1000 |

In the heteroatom replacement, O-analog 9 retained folate receptor and KB cell activity, however S-analog 10 showed no anti-tumor activity. 11 with the region-isomeric replacement gave a total loss in activity and uptake. With no improvement in activity, the compounds were not tested further for enzyme inhibition. The data however proves our hypothesis that the distance and orientation of the pyrrolo pyrimide scaffold with respect to the glutamate side chain is crucial for selectivity as well as anti-tumor activity.

A novel series of classical 5-substituted pyrrolo[2,3-d] pyrimidines (compounds 9-11) were designed and tested for antifolate anti-cancer activity with tumor targeted uptake. The data presented show that minute changes in bond angle and bond length between the glutamate side chain and the pyrrolo pyrimidine scaffold drastically affect selective uptake and cytotoxic activity.

Novel Synthetic Methodology for 5- and 6-Substituted Cyclopenta[d]Pyrimidine for Potential Nonclassical and Classical Antifolates as TS and DHFR Inhibitors (Schemes 3-6)

Figure 3:
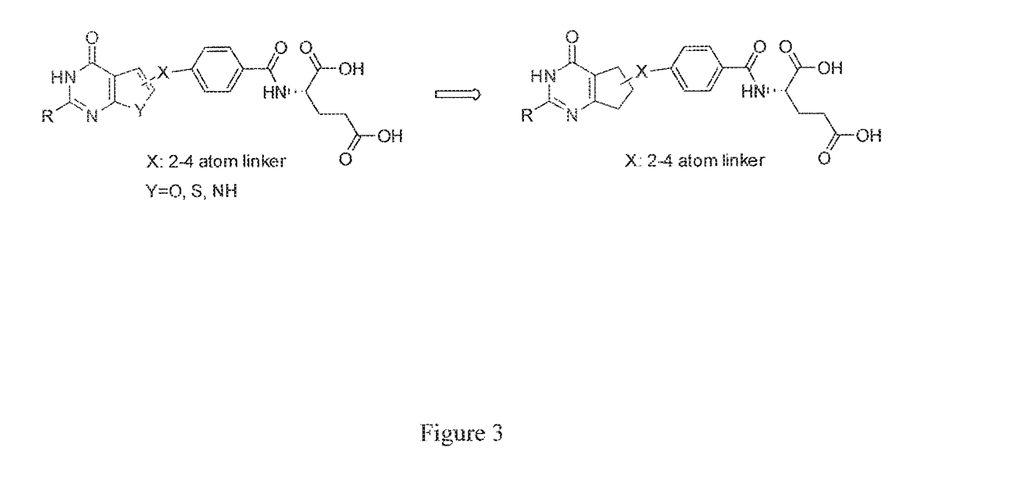
FIG. 3 shows lead compounds and designed target compounds of this invention.

We have reported several thieno[2,3-d]pyrimidine[19], pyrrolo[2,3-d]pyrimidine[20], furo[2,3-d]pyrimidine[21]. FIG. 3 shows classical antifolates as selective tumor targeting agents. These agents are selectively transported by the folate receptor (FR) and/or proton-coupled folate transporter (PCFT) rather than the ubiquitous reduced folate carrier (RFC). These compounds inhibit FR and PCFT expressing tumor cells (KB and IGROV1) at picomolar to nanomolar IC$_{50}$ values. It is suggested in the literature,[20,21] for classical antifolates, that a heteroatom in the 7-position of pyrimidine-fused five member rings or the 8-position of pyrimidine-fused six member rings may play a crucial role in drug uptake. Although the literature is surfeit with the synthesis of fused pyrimidine bicyclic and tricyclic analogs, a viable synthetic method for substituted cyclopenta[d]pyrimidine analogs is conspicuously absent. As part of our continuing efforts to synthesize molecules with targeted tumor-specific attributes and to obtain a broad SAR, we set forth in this invention a novel synthetic methodology for synthesizing 5- and 6-substituted cyclopenta[d]pyrimidine nonclassical and classical antifolates (see FIG. 3).

Chemistry

Scheme 3. Metathesis reaction failed to synthesize the target compound.

We first attempted the synthesis of a two carbon linker target compound 1 (Scheme 3) by olefin metathesis. In this attempt, we started from the commercial available epoxide (compound 2, Scheme 3) which when treated with conc HCl afforded diol (compound 3, Scheme3) in 85% yield. Tris (cetylpyridinium) 12-tungstophosphate (CWP) catalyzed oxidation of compound 3, Scheme 3, with H$_2$O$_2$ gave ethylene hexanedioic acid compound 4, Scheme3, in 60% yield. Chlorination of compound 4, Scheme3, with oxalyl chloride and subsequently methylation afforded the dimethyl ester (compound 5, Scheme 3) in 70% yield. Cyclization of compound 5, Scheme3, with acetamidine and potassium tertbutoxide in DMF provided ethylene cyclopenta[d] pyrimidine (compound 6, Scheme 3) in 50% yield. Different conditions including Grubbs I[22] and II[23] failed to provide metathesis of compound 6, Scheme3, with 4-methoxycarbonyl styrene. These failures were probably due to the conjugated olefin with the phenyl ring in styrene.

Scheme 4. Synthesis of cyclopenta[d]pyrimidine scaffold.

Scheme 5. Reduction of compound 12 (Scheme 5), and separation of compounds 13a and 13b, Scheme 5.

separated by column due to polarity difference
(13a has low polarity resulting from intramolecular H-B)

Reduction of ester moieties in the compounds 12a and 12b, Scheme 5, mixture with excess DIBALH at −30° C. afforded the hydroxy group. In the 5-hydroxyl regioisomer 13a, Scheme 5, the hydroxyl group formed an intramolecular hydrogen bond with the 4-oxo. This did not occur with the regioisomer 13b, Scheme 5. Thus intramolecular hydrogen bond resulted in significantly lower polarity of 13a compared with 13b, Scheme 5, (TLC (CHCl3/MeOH, 10:1), Rf 0.45 of 13a vs 0.15 of 13b). Separation of compounds 13a and 13b, Scheme 5, was achieved by silca gel column chromatography in 42% and 40% isolated yields respectively.

We designed an alternate new route in Scheme 4 (novel method of this invention) to provide a functionalization handle, ethoxycarbonyl group, attached at 5- or 6-position of the cyclopenta[d]pyrimidine. Commercially available tricarboxylic acid (compound 8, Scheme 4) treated with oxalyl chloride and a catalytic amount of DMF afforded tricarbonyl chloride (compound 9, Scheme 4) in 95% yield. Triethyl esterification of compound 9, Scheme 4, with anhydrous ethanol in toluene gave the triethyl carboxylate (compound 10, Scheme 4) in almost quantitative yield. Cyclization of compound 10, Scheme4, with sodium ethoxide in toluene provided two diethoxycarbonyl cyclopentones compounds 11a and 11b, Scheme 4, mixture in 88% total yield. Cyclization of the mixture of compounds 11a and 11b regioisomers (Scheme 4) with acetamidine afforded a mixture of cyclopenta[d]pyrimidines (compounds 12a and 12b, Scheme 4) in 91% total yield.

Scheme 6. Synthesis of the target compound 18b.

We synthesized one of our antifolate target compounds 18b<Scheme 6, from 13b (Schemes 5, and 6) as an example to demonstrate the feasibility of the functional modulation of the hydroxyl handle that we installed on the cyclopenta ring. Nosylation of both hydroxyl and oxo of 13b (Scheme 6) with NsCl and TEA and catalytic DMAP in DCM gave dinosylated compound 14b (Scheme 6) in 85% yield. Selective nucleophilic displacement of the 6-Ns in compound 14b (Scheme 6) with ethyl 4-hydroxy benzoic acid ester, cesium carbonate and molecular sieves in acetonitrile provided the pteroic ester (compound 15b, Scheme 6) in 70% isolated yield. Hydrolysis of compound 15b, Scheme 6, with 1N KOH gave pteroic acid compound 16b, Scheme 6, in 70% yield. Peptide coupling of compound 16b, Scheme 6, with L-glutamic acid ester and coupling reagents CDMT and NMM in DMF afforded compound 17b, Scheme 6, in 65% yield. Hydrolysis of compound 17b, Scheme 6, in 1N NaOH provided target compound 18b, Scheme 6, in 90% yield.

Those persons skilled in the art shall appreciate that the present invention provides a novel viable synthetic methodology for cyclopenta[d]pyrimidine classical antifolates. In this synthetic route of the method of this invention, we separated the 5- and 6-regioisomers by polarity difference of hydroxy group with and without intramolecular hydrogen bond capability. The hydroxy group serves as a versatile handle, which can be utilized to synthesize other novel 5- and 6-substituted compounds of pharmacological interests. Compound 18b of Scheme 6, of this invention, is an effective inhibitor of folate metabolizing enzymes antiproliferation agents and for the inhibition of tumor cells in culture.

REFERENCES

1. Mitchell-Ryan, H.; Wang, Y.; Raghavan, S.; Ravindra, M. P.; Hales, H.; Orr, S.; Cherian, C.; Hou, Z.; Matherly, L. H.; Gangjee, A. Discovery of 5-Substituted Pyrrolo[2,3-d]pyrimidine Antifolates as Dual-Acting Inhibitors of Glycinamide Ribonucleotide Formyltransferase and 5-Aminoimidazole-4-carboxamide Ribonucleotide Formyltransferase in De Novo Purine Nucleotide Biosynthesis: Implications of Inhibiting 5-Aminoimidazole-4-carboxamide Ribonucleotide Formyltransferase to AMPK Activation and Anti-Tumor activity. *J. Med. Chem* 2013, 56, 10016-10032.
2. Elnakat, H.; Ratnam, M. Distribution, functionality and gene regulation of folate receptor isoforms: implications in targeted therapy. *Adv Drug Deliv Rev* 2004, 56, 1067-1084.
3. Nakai, Y.; Inoue, K.; Abe, N.; Hatakeyama, M.; Ohta, K.; Otagiri, M.; Hayashi, Y.; Yuasa, H. Functional characterization of human proton-coupled folate transporter/heme carrier protein 1 heterologously expressed in mammalian cells as a folate transporter. *J Pharmacol Exp Ther* 2007, 322, 469-476.
4. Qiu, A.; Jansen, M.; Sakaris, A.; Min, S.; Chattopadhyay, S.; Tsai, E.; Sandoval, C.; Zhao, R.; Akabas, M.; Goldman, I. D. Identification of an intestinal folate transporter and the molecular basis for hereditary folate malabsorption. *Cell* 2006, 127, 917-928.
5. Qiu, A.; Min, S.; Jansen, M.; Malhotra, U.; Tsai, E.; Cabelof, D.; Matherly L. H., Zhao, R.; Akabas, M.; Goldman, I. D. Rodent intestinal folate transporters (SLC46A1): secondary structure, functional properties, and response to dietary folate restriction. *Am J Physiol Cell Physiol* 2007, 293, 1669-1678.
6. Matherly, L. H.; Hou, Z.; Deng, Y. Human Reduced Folate Carrier: Translation Of Basic Biology To Cancer Etiology And Therapy. *Cancer and Metastasis Reviews* 2007, 26, 111-128.
7. Zhao, R.; Goldman, I. D. Resistance To Antifolates. *Oncogene* 2003. 22, 7431-7457.
8. Baldwin, S., W.; Taylor, E., C. et al. Structural Features of 5,10-Dideaza-5,6,7,8-tetrahydrofolat That Determine Inhibition of Mammalian Glycinamide Ribonucleotide Formyltransferase. *Biochemistry* 1991, 30, 1997-2006.
9. Shahade, D. A. PCT Int. Appl., 2008072652, 2008.
10. Salvatore, R. N.; Smith, R. A.; Nischwitz, A. K.; Gavin, T. A mild and highly convenient chemoselective alkylation of thiols using Cs2CO3-TBAI. *Tetrahedron Letters* 2005, 46, 8931-8935.
11. Raghavan, S.; Kumar, V. V. Stereoselective synthesis of the C1-C8 subunit of peloruside A. *Tetrahedron* 2013, 69, 4835-4844.
12. Kanao, M.; Watanabe, Y.; Kimura, Y.; Kanno, H.; Kubo, H.; Ashida, S. Thromboxane A2 synthetase inhibitors. I. Syntheses and activities of various N-heteroaromatic derivatives. *Chem. Pharm. Bull* 1988, 36, 2968-76.

13. Matherly, L. H.; Hou, Z.; Deng, Y. Human Reduced Folate Carrier: Translation of Basic Biology to Cancer Etiology and Therapy. *Cancer Metastasis Rev.* 2007, 26, 111-128.
14. Elnakat, H.; Ratnam, M. Distribution, Functionality and Gene Regulation of Folate Receptor Isoforms: Implications in Targeted Therapy. *Adv. Drug Dev.* 2004, 56, 1067-1084
15. Zhao, R.; Matherly, L. H.; Goldman, I. D. Membrane Transporters and Folate Homeostasis; Intestinal Absorption, Transport into Systemic Compartments and Tissues. *Expert Rev. Mol. Med.* 2009, 11, e4.
16. Zhao, R.; Goldman, I. D. The Molecular Identity and Characterization of a Proton-Coupled Folate Transporter-PCFT; Biological Ramifications and Impact on the Activity of Pemetrexed. *Cancer Metastasis Rev.* 2007, 26, 129-139.
17. Kugel Desmoulin, S.; Wang, Y.; Tait, L.; Hou, Z.; Cherian, C.; Gangjee, A.; Matherly, L. H. Expression Profiling of the Major Folate Facilitative Transporters in Human Tumors and Normal Tissues Abstr., *Am. Assoc. Cancer Res.* 2010, 51, 1103.
18. Qiu, A.; Min, S. H.; Jansen, M.; Malhotra, U.; Tsai, E.; Cabelof, D. C.; Matherly, L. H.; Zhao, R.; Akabas, M. H.; Goldman, I. D. Rodent Intestinal Folate Transporters (SLC46A1): Secondary Structure, Functional Properties, and Response to Dietary Folate Restriction. *Am. J. Physiol.: Cell Physiol.* 2007, 293, 1669-1678.
19. Deng, Y.; Zhou, X.; Desmoulin, S. K.; Wu, J.; Cherian, C.; Hou, Z.; Matherly, L. H; Gangjee, A. Synthesis and Biological Activity of a Novel Series of 6-Substituted Thieno[2,3-d]pyrimidine Antifolate Inhibitors of Purine Biosynthesis with Selectivity for High Affinity Folate Receptors over the Reduced Folate Carrier and Proton-Coupled Folate Transporter for Cellular Entry. *J. Med. Chem.* 2009, 52, 2940-2951.
20. Wang, L.; Cherian, C.; Desmoulin, S. K.; Ran, S. M.; Hou, Z.; Matherly, L. H.; Gangjee, A. Synthesis and Biological Activity of 6-Substituted Pyrrolo[2,3-d]pyrimidine Thienoyl Regioisomer as Inhibitors of de Novo Purine Biosynthesis with Selectivity for Cellular Uptake by High Affinity Folate Receptors and Proton-Coupled Folate Transporter Over the Reduced Folate Carrier. *J. Med. Chem.* 2012, 55, 1758-1770.
21. Gangjee, A.; Zeng, Y.; McGuire, J. J.; Kisliuk, R. L. Synthesis of Classical, Four-Carbon Bridged 5-Substituted Furo[2,3-d]pyrimidine and 6-Substituted Pyrrolo[2,3-d]pyrimidine Analogues as Antifolates. *J. Med. Chem.* 2005, 48, 5329-5336.
22. Chatterjee, A. K.; Choi, T. L.; Sanders, D. P.; Grubbs, R. H. A General Model for Selectivity in Olefin Cross Metathesis. *J. A. C. S.* 2003, 125, 11360-11370.
23. Galan, B. R.; Kalbarczyk, K. P.; Szczepankiewicz, S.; Keister, J. B.; Diver, S. T. A Rapid and Simple Cleanup Procedure for Metathesis Reactions. *Org. Lett.,* 2007, 9, 1203-1206.

It will be appreciated by those persons skilled in the art that changes could be made to the embodiments described above without departing from the broad inventive concept thereof. It is understood therefore, that this invention is not limited to the particular embodiments disclosed, but it is intended to cover modifications that are within the spirit and scope of the invention, as defined by the appended claims.

What is claimed is:

1. A method of treating a patient having cancer selected from the group consisting of Malignant Pleural Mesothelioma and Non-Small Cell Lung Cancer, comprising administering to the patient an effective amount of a compound of a formula:

wherein X is O and n is three, and optionally comprising a pharmaceutically acceptable salt, hydrate, or solvate thereof, and including optionally administering an effective amount of said salt, hydrate, or solvate of said compound to said patient.

* * * * *